United States Patent [19]   [11] 4,208,523
Michne et al.   [45] Jun. 17, 1980

[54] 11-LOWER-ALKYL-, 11-PHENYL-LOWER-ALKYL- AND 11-CYCLO-LOWER-ALKYL-LOWER-ALKYL-HEXAHYDRO-2,6-METHANO-3-BENZAZOCINES

[75] Inventors: William F. Michne, Poestenkill; Thomas R. Lewis, Bethlehem, both of N.Y.

[73] Assignee: Sterling Drug Inc., New York, N.Y.

[21] Appl. No.: 964,915

[22] Filed: Nov. 30, 1978

[51] Int. Cl.$^2$ ............................................. C07D 221/26
[52] U.S. Cl. ...................................... 546/97; 424/267; 546/74
[58] Field of Search ........................................ 546/97, 74

[56] References Cited

U.S. PATENT DOCUMENTS

| 3,733,330 | 5/1973 | Schubert et al. | 546/97 |
| 3,764,606 | 10/1973 | Akkerman et al. | 546/97 |
| 3,969,468 | 7/1976 | Tamaki et al. | 546/97 |
| 3,981,874 | 9/1976 | Merz et al. | 546/97 |
| 4,020,164 | 4/1977 | Rahtz et al. | 546/97 |
| 4,128,548 | 12/1978 | Akkerman et al. | 546/97 X |

OTHER PUBLICATIONS

Ager, J., et al., *J. Med. Chem.*, 6, 322–325, (1963).
Rice, K., et al., *J. Med. Chem.*, 18, 854–857, (1975).
Fieser, L., et al., *Reagents for Organic Synthesis*, John Wiley, New York, 1967, p. 435.
March, J., *Advanced Organic Chemistry*, McGraw Hill, New York, 1968, pp. 319–320.

*Primary Examiner*—Henry R. Jiles
*Assistant Examiner*—Richard A. Schwartz
*Attorney, Agent, or Firm*—William G. Webb; B. Woodrow Wyatt

[57] ABSTRACT

3-$R_1$-7-$R_2''$-8-$R_2$-9-$R_2'$-10-$R_2'''$-11(ax)-$R_3$-6(eq)-$R_4$-11(eq)-($CH_2CH_2CH_2R_5$)-1,2,3,4,5,6-hexahydro-2,6-methano-3-benzazocines, generally useful as morphine-like analgesics and as narcotic antagonists, are prepared by reducing, under Wolff-Kishner reaction conditions, a corresponding 3-$R_1$-7-$R_2''$-8-$R_2$-9-$R_2'$-10-$R_2'''$-11(ax)-$R_3$-6(eq)-$R_4$-11(eq)-($CH_2CH_2COR_5$)-1,2,3,4,5,6-hexahydro-2,6-methano-3-benzazocine and, if desired, cleaving a lower-alkoxy, methoxymethoxy or benzyloxy group to an hydroxy group.

20 Claims, No Drawings

11-LOWER-ALKYL-, 11-PHENYL-LOWER-ALKYL- AND 11-CYCLO-LOWER-ALKYL-LOWER-ALKYL-HEXAHYDRO-2,6-METHANO-3-BENZAZOCINES

BACKGROUND OF THE INVENTION (a) Field of the Invention

This invention relates to certain 11(eq)-($CH_2CH_2CH_2$-$R_5$)-hexahydro-2,6-methano-3-benzazocines, generally useful as morphine-like analgesics and as narcotic antagonists.

(b) Description of the Prior Art

There are several references in the literature, especially the patent literature, to 1,2,3,4,5,6-hexahydro-2,6-methano-3-benzazocines having lower-alkyl substituents containing up to six carbon atoms in a side chain attached to the 11-position of the hexahydro-2,6-methano-3-benzazocine nucleus. However, these references specifically disclose only 11-methyl-substituted benzazocines (Akkerman et al. U.S. Pat. No. 3,764,606 and Schubert et al. U.S. Pat. No. 3,733,330); or 11-methyl and 11-ethyl-substituted compounds (Merz et al. U.S. Pat. No. 3,981,874). There are no known references, either in the scientific or the patent literature, which disclose such hexahydro-2,6-methano-3-benzazocines having 11-alkyl chains containing four or more carbon atoms, and there are only occasional species of 1,2,3,4,5,6-hexahydro-2,6-methano-3-benzazocines specifically disclosed in the patent literature where the 11-alkyl side chain contains a three carbon group, i.e. propyl (for example Rahtz et al. U.S. Pat. No. 4,020,164, column 7, lines 26–27). Ager et al., J. Med. Chem., 6 (3), 322–325 (1963) and Rice et al., J. Med. Chem., 18 (8), 854–857 (1975), disclose that, by increasing the bulk (i.e. the chain length) of 9-lower-alkyl-6,7-benzomorphans (or named as 11-lower-alkyl-1,2,3,4,5,6-hexahydro-2,6-methano-3-benzazocines using alternative nomenclature), the potency is diminished as the lower-alkyl group is lengthened from methyl to ethyl to propyl.

SUMMARY OF THE INVENTION

In a composition of matter aspect, the present invention relates to 3-$R_1$-7-$R_2''$-8-$R_2$-9-$R_2'$-10-$R_2'''$-11(ax)-$R_3$-6(eq)-$R_4$-11(eq)-($CH_2CH_2CH_2R_5$)-1,2,3,4,5,6-hexahydro-2,6-methano-3-benzazocines, wherein $R_1$ is lower-alkyl, lower-alkenyl, cyclo-lower-alkyl-lower-alkyl, hydrogen or benzyl; one of $R_2$, $R_2'$, $R_2''$ and $R_2'''$ is hydroxy, lower-alkoxy, methoxymethoxy, benzyloxy or lower-alkanoyloxy, the others being hydrogen; $R_3$ is hydrogen or lower-alkyl; $R_4$ is lower-alkyl, or $R_3$ and $R_4$ together represent lower-alkylene, $(CH_2)_n$, where n is one of the integers 3 or 4; and $R_5$ is lower-alkyl, phenyl, phenyl-lower-alkyl, cyclo-lower-alkyl or cycloalkyl-lower-alkyl, or such phenyl and phenyl-lower-alkyl groups substituted in the phenyl ring by a lower-alkyl group. These compounds are generally useful as morphine-like analgesics and as narcotic antagonists, and one species has been found to have a highly unusual profile of analgesic activity never before observed with any known class of strong analgesics.

DETAILED DESCRIPTION INCLUSIVE OF THE PREFERRED EMBODIMENTS

More specifically, this invention provides compounds having the formula:

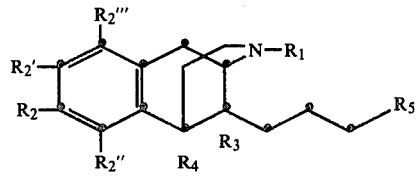

I and chemically designated 3-$R_1$-7-$R_2''$-8-$R_2$-9-$R_2'$-10-$R_2'''$-11(ax)-$R_3$-6(eq)-$R_4$-11(eq)-($CH_2CH_2CH_2R_5$)-1,2,3,4,5,6-hexahydro-2,6-methano-3-benzazocines, which are generally useful as morphine-like analgesics and as narcotic antagonists, one species having non-morphine-like analgesic activity, and where $R_1$ is lower-alkyl, lower-alkenyl, cyclo-lower-alkyl-lower-alkyl, hydrogen or benzyl; one of $R_2$, $R_2'$, $R_2''$ and $R_2'''$ is hydroxy, lower-alkoxy, methoxymethoxy, benzyloxy or lower-alkanoyloxy, the others being hydrogen; $R_3$ is hydrogen or lower-alkyl; $R_4$ is lower-alkyl, or $R_3$ and $R_4$ together represent lower-alkylene, $(CH_2)_n$, where n is one of the integers 3 or 4; and $R_5$ is lower-alkyl, phenyl, phenyl-lower-alkyl, cyclo-lower-alkyl or cyclo-lower-alkyl-lower-alkyl, or such phenyl and phenyl-lower-alkyl groups substituted in the phenyl ring by a lower-alkyl group.

Preferred species within the ambit of the invention are those as defined above where $R_2$ is hydroxy or lower-alkoxy, $R_2'$, $R_2''$ and $R_2'''$ being hydrogen; $R_1$ is lower-alkyl; $R_3$ is hydrogen or lower-alkyl; $R_4$ is lower-alkyl; and $R_5$ is lower-alkyl, phenyl or phenyl-lower-alkyl or such phenyl or phenyl-lower-alkyl groups substituted in the phenyl ring by a lower-alkyl group. Particularly preferred species of the latter group are those where $R_5$ as lower-alkyl contains from three to six carbon atoms in the lower-alkyl group.

As used herein, the terms lower-alkyl, lower-alkoxy and lower-alkanoyl mean saturated, acyclic groups which may be straight or branched containing from one to about eight carbon atoms as exemplified by methyl, ethyl, propyl, isopropyl, butyl, octyl, methoxy, ethoxy, propoxy, isopropoxy, butoxy, octyloxy, formyl, acetyl, butyryl, α-methylbutyryl or octanoyl.

As used herein, the term lower-alkenyl means acyclic groups, which may be straight or branched, containing from three to about seven carbon atoms and having one double bond, as exemplified by 1-(2-propenyl), 1-(2-methyl-2-propenyl), 1-(2-butenyl), 1-(3-methyl-2-butenyl) or 1-(3-ethyl-2-pentenyl).

As used herein the term cyclo-lower-alkyl means saturated, carbocyclic groups having from three to seven ring carbon atoms as exemplified by cyclopropyl, cyclobutyl, cyclopentyl, 2-methylcyclopentyl, 2,3-dimethylcyclopentyl, cyclohexyl or cycloheptyl.

The compounds of formula I are prepared by reduction, under Wolff-Kishner reaction conditions, of a corresponding 3-$R_1$-7-$R_2''$-8-$R_2$-9-$R_2'$-10-$R_2'''$-11(ax)-$R_3$-6(eq)-$R_4$-11(eq)-($CH_2CH_2COR_5$)-1,2,3,4,5,6-hexahydro-2,6-methano-3-benzazocine having the formula II:

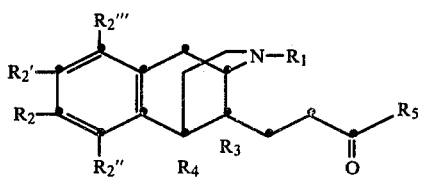

II where $R_1$, $R_2$, $R_2'$, $R_2''$, $R_2'''$, $R_3$, $R_4$ and $R_5$ have the meanings given above. The reaction is carried out by heating the compounds of formula II with hydrazine and an alkali metal hydroxide, for example sodium hydroxide or potassium hydroxide, in an organic solvent inert under the conditions of the reaction, preferably a lower-alkylene glycol or a poly-lower-alkylene glycol, such as ethylene glycol, diethylene glycol or propylene glycol, at a temperature from 100° to 250° C. During the course of the reaction, any ether groups present in the molecule, for example any $R_2$, $R_2'$, $R_2''$ or $R_2'''$ group as lower-alkoxy, methoxymethoxy or benzyloxy, are susceptible to cleavage to the corresponding hydroxy groups, and such cleavage is generally favored by prolonged reaction times. The reduction of the 11-$CH_2CH_2COR_5$ group is usually completed in from one to about five hours. Therefore if it is desired to produce compounds of formula I where one of $R_2$, $R_2'$, $R_2''$ or $R_2'''$ is lower-alkoxy, methoxymethoxy or benzyloxy from the corresponding ethers of formula II, or if it is desired to produce a compound of formula I from a compound of formula II where the $R_2$, $R_2'$, $R_2''$ or $R_2'''$ group in both the starting material and the product is hydroxy, it is preferred to use a reaction time from one to about seven hours. By the same token, the compounds of formula I where one of $R_2$, $R_2'$, $R_2''$ or $R_2'''$ is hydroxy are also prepared by use of starting materials of formula II where one of the $R_2$, $R_2'$, $R_2''$ and $R_2'''$ groups is hydroxy, lower-alkoxy, methoxymethoxy or benzyloxy and a reaction time from around twenty to around thirty hours. In either case, the course of the reaction, and the formation of the hydroxy compounds from the corresponding ethers can be followed by thin layer chromatographic analyses at intervals during the reaction, and the reaction can be either terminated or continued according to whether ether cleavage is desired or not.

The compounds of formula II, and methods for their preparation, are described in Michne, U.S. Pat. No. 4,100,164 and in Lewis and Michne, U.S. Pat. No. 4,119,628, the disclosures of which are incorporated herein by reference.

Of course, the compounds of formula I where one of $R_2$, $R_2'$, $R_2''$ or $R_2'''$ is hydroxy can also be advantageously prepared by cleavage of a corresponding compound of formula I where one of $R_2$, $R_2'$, $R_2''$ and $R_2'''$ is lower-alkoxy, methoxymethoxy or benzyloxy by cleavage of the latter either with hydrogen bromide or with sodium propyl sulfide using procedures well known in the art.

The compounds of formula I where one of $R_2$, $R_2'$, $R_2''$ and $R_2'''$ is lower-alkanoyloxy are preferably prepared by esterification of the corresponding compounds where a respective one of $R_2$, $R_2'$, $R_2''$ and $R_2'''$ is hydroxy with a lower-alkanoic acid anhydride or with a lower-alkanoyl halide in the presence of an appropriate acid-acceptor and, if appropriate, in a suitable organic solvent. When an acid anhydride is used for the esterification, the reaction is preferably carried out in an excess of pyridine, which serves both as a solvent and as an acid-acceptor. When an acid halide is used as the esterification reagent, the reaction is preferably carried out in an inert organic solvent, such as benzene, toluene or methylene dichloride, in the presence of a tri-lower-alkylamine as the acid-acceptor.

The compounds of formula I where one of $R_2$, $R_2'$, $R_2''$ and $R_2'''$ is lower-alkoxy or benzyloxy can also be prepared from the corresponding compounds where a respective one of $R_2$, $R_2'$, $R_2''$ and $R_2'''$ is hydroxy by reaction of the latter with a strong base, for example an alkali metal amide or an alkali metal hydride, and reaction of the resulting alkali metal salt with a lower-alkyl or benzyl ester of a strong inorganic acid, for example a lower-alkyl or benzyl halide or a di-lower-alkyl sulfate, in an inert organic solvent, for example dimethylformamide (DMF).

The compounds of formula I where one of $R_2$, $R_2'$, $R_2''$ and $R_2'''$ is methoxymethoxy are preferably prepared from the corresponding compounds where a respective one of $R_2$, $R_2'$, $R_2''$ and $R_2'''$ is hydroxy by reaction of the latter with dimethoxymethane. The reaction is carried out by refluxing a solution of the starting material of formula I in dimethoxymethane in the presence of a catalytic amount of p-toluenesulfonic acid using a Soxhlet extractor having in the thimble thereof molecular sieves of a porosity sufficiently large to hold molecules of methanol which is produced in the reaction. The molecular sieves of such porosity also serve to trap any water present in the reaction mixture, and the reaction is thus carried out under anhydrous conditions. It has been found that a 4A molecular sieve is suitable for the stated purposes.

The compounds of formula I where $R_1$ is benzyl or hydrogen are useful as intermediates for preparing the compounds where $R_1$ is lower-alkyl, lower-alkenyl or cyclo-lower-alkyl-lower-alkyl. Thus the compounds of formula I where $R_1$ is benzyl are catalytically debenzylated with hydrogen over a suitable catalyst, for example palladium-on-charcoal or Raney nickel, in an inert organic solvent, for example a lower-alkanol, and the resulting debenzylated compounds are realkylated with a lower-alkyl, lower-alkenyl or cyclo-lower-alkyl-lower-alkyl halide in the presence of an acid-acceptor, for example an alkali metal carbonate, in a suitable inert organic solvent, for example dimethylformamide or a lower-alkanol.

Due to the presence of a basic amino grouping, the free base forms represented by formula I above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsenic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base forms, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of this invention can exist in enantiomeric forms separable into enantiomers. If desired, the isolation or the production of a particular enantiomeric form can be accomplished by application of general principles known in the prior art. In the nomenclature employed for the compounds of formula I herein, "ax" stands for axial and "eq" for equatorial, and the configurations are given with reference to the hydroaromatic ring. Thus, the 6(eq), 11(ax) compounds of formula I are in the cis configuration, whereas the 6(eq), 11(eq) compounds are in the trans configuration.

In standard pharmacological test procedures, the compounds of formula I and the acid-addition salts thereof have been found useful as depressants of the central nervous system, and more particularly have been found useful as analgesics and as antagonists of strong analgesics such as phenazocine, meperidine and morphine.

The compounds of formula I can be administered in the same manner as known analgesics and antagonists of strong analgesics, i.e. parenterally or orally in any of the conventional pharmaceutical forms, as for instance solutions, suspensions, tablets, capsules, and the like.

The useful properties of the compounds of this invention were demonstrated by standard pharmacological procedures readily carried out by technicans having ordinary skill in pharmacological test procedures, so that the actual determination of numerical biological data definitive for a particular test compound can be ascertained without the need for any extensive experimentation.

The test procedures used to determine the analgesic and narcotic antagonist activities of the compounds of the invention have been described in detail in the prior art and are as follows: The acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exp. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol. 18, 135 (1966); the phenyl-p-quinone-induced writhing test, also a primary analgesic screening test, designed to measure the ability of a test agent to prevent phenyl-p-quinone-induced writhing in mice, described by Pearl and Harris, J. Pharmacol. Exptl. Therap. 154, 319–323 (1966); the rat tail flick radiant thermal heat analgesic (agonist) test described by D'Amour and Smith, J. Pharmacol. Exptl. Therap. 72, 74 (1941) as modified by Bass and Vander-Brook, J. Am. Pharm. Assoc. Sci. Ed. 41, 569 (1956); the phenazocine antagonist test, which is designed to measure the ability of a test agent to antagonize the effect of phenazocine in the above-identified rat tail flick response test, described by Harris and Pierson, J. Pharmacol. Exptl. Therap. 143, 141 (1964); and the Straub tail test which is an observation of erection and arching of the tail in mice and which is characteristic of narcotic analgesics, such as morphine, first described by Straub, Dtsch. med. Wochr. (1911), page 1426 and further described by Aceto et al., Brit. J. Pharmacol. 36, 225–239 (1969).

The structures of the compounds of this invention were established by the modes of synthesis, by elementary analyses and by ultraviolet, infrared and nuclear magnetic resonance spectra. The course of reactions and homogeneity of the products were ascertained by thin layer chromatography.

The manner and process of making and using the invention, and the best mode contemplated by the inventors of carrying out this invention, will now be described so as to enable any person skilled in the art to which it pertains to make and use the same. The melting points are uncorrected.

EXAMPLE 1

A. A mixture of 7.5 g. (0.02 mole) of 8-methoxy-3,6(eq),11(ax)-trimethyl-1,2,3,4,5,6-hexahydro-11(eq)-(3-oxo-6-methylheptyl)-2,6-methano-3-benzazocine, 20 ml. of 100% hydrazine hydrate and 5.3 g. (0.08 mole) of potassium hydroxide pellets in 50 ml. of diethylene glycol was heated with stirring in an oil bath at 200°–210° C. for about two hours and then allowed to cool to ambient temperature.

The mixture was diluted with 300 ml. of water, extracted three times with diethyl ether, and the combined extracts were washed twice with water, once with brine, dried, filtered and taken to dryness in vacuo to give 6.7 g. of 8-methoxy-3,6(eq),11(ax)-trimethyl-1,2,3,4,5,6-hexahydro-11(eq)-(6-methylheptyl)-2,6-methano-3-benzazocine as a syrup.

The latter, without further purification, was dissolved in 70 ml. of 48% aqueous hydrobromic acid, and the solution was stirred and refluxed for one hour. The reaction mixture was then cooled, neutralized by the addition of 70 ml. of concentrated ammonium hydroxide and extracted twice with 70 ml. portions of methylene dichloride. The combined extracts were washed with water, dried, filtered and evaporated to dryness to give 5.5 g. of crude product which, after repeated recrystallizations from ethanol, afforded 2.2 g. of 8-hydroxy-3,6(eq),11(ax)-trimethyl-1,2,3,4,5,6-hexahydro-11(eq)-(6-methylheptyl)-2,6-methano-3-benzazocine, m.p. 153°–157° C.

Following a procedure similar to that described in Example 1A above, the following compounds of formula I were similarly prepared:

B. Heating 2.8 g. (0.008 mole) of 8-methoxy-3,6(eq)-dimethyl-1,2,3,4,5,6-hexahydro-11(eq)-(3-oxoheptyl)-2,6-methano-3-benzazocine with 8.2 ml. of 100% hydrazine hydrate and 2.3 g. (0.04 mole) of powdered potassium hydroxide in 20.4 ml. of diethylene glycol for one and one half hours at 215° C. and isolation of the product in the form of the free base gave 2.2 g. of 8-methoxy-3,6(eq)-dimethyl-1,2,3,4,5,6-hexahydro-11(eq)-heptyl-2,6-methano-3-benzazocine as a syrup which, on heating with 22 ml. of 48% hydrobromic acid and isolation of the product in the form of the hydrochloride salt, gave 2.1 g. of 8-hydroxy-3,6(eq)-dimethyl-1,2,3,4,5,6-hexahydro-11(eq)-heptyl-2,6-methano-3-benzazocine hydrochloride m.p. 230°–233° C. (from ethanol).

C. Heating 6.7 g. (0.019 mole) of 8-methoxy-3,6(eq)-dimethyl-1,2,3,4,5,6-hexahydro-11(eq)-(3-oxo-6-methylheptyl)-2,6-methano-3-benzazocine with 18.8 ml. of 100% hydrazine hydrate and 5.3 g. (0.094 mole) of powdered potassium hydroxide in 46.9 ml. of diethylene glycol for one and one-half hours at 220° C. and isolation of the product in the form of the free base gave 6.4 g. of 8-methoxy-3,6(eq)-dimethyl-1,2,3,4,5,6-hexahydro-11(eq)-(6-methylheptyl)-2,6-methano-3-benzazocine as a syrup which, on heating with 64 ml. of 48% hydrobromic acid, afforded 1.8 g. of 8-hydroxy-3,6(eq)-dimethyl-1,2,3,4,5,6-hexahydro-11(eq)-(6-methylheptyl)-2,6-methano-3-benzazocine, m.p. 150°–152° C. (from ethanol).

D. Heating 4.7 g. (0.01 mole) of 8-methoxy-3,6(eq), 11 (ax)-trimethyl-1,2,3,4,5,6-hexahydro-11(eq)-(3-oxoheptyl)-2,6-methano-3-benzazocine with 13.1 ml. of 100% hydrazine hydrate and 3.7 g. (0.066 mole) of powdered potassium hydroxide in 32.8 ml. of diethylene glycol for two hours at 220° C. and isolation of the product in the form of the free base gave 4.1 g. of 8-methoxy-3,6(eq),11(ax)-trimethyl-1,2,3,4,5,6-hexahydro-11(eq)-heptyl-2,6-methano-3-benzazocine as a syrup which, on heating with 41 ml. of 48% hydrobromic acid, gave 1.9 g. of 8-hydroxy-3,6(eq),11(ax)-trimethyl-1,2,3,4,5,6-hexahydro-11(eq)-heptyl-2,6-methano-3-benzazocine, m.p. 169°–172° C. (from ethanol).

E. Heating 9.7 g. (0.028 mole) of 8-methoxy-3,6(eq), 11 (ax)-trimethyl-1,2,3,4,5,6-hexahydro-11(eq)-(3-oxohexyl)-2,6-methano-3-benzazocine with a solution of 10.2 ml. of hydrazine in 5.8 ml. of water and 6.4 g. of powdered potassium hydroxide in 78 ml. of diethylene glycol for two hours at 205° C. and isolation of the product in the form of the free base afforded 8.5 g. of 8-methoxy-3,6(eq),11(ax)-trimethyl-1,2,3,4,5,6-hexahydro-11(eq)-hexyl-2,6-methano-3-benzazocine, as a syrup which, on heating with 85 ml. of 48% hydrobromic acid, gave 4.1 g. of 8-hydroxy-3,6(eq),11(ax)-trimethyl-1,2,3,4,5,6-hexahydro-11(eq)-hexyl-2,6-methano-3-benzazocine, m.p. 181°–184° C. (from ethanol).

F. Heating 7.0 g. (0.019 mole) of 8-methoxy-3,6(eq), 11 (ax)-trimethyl-1,2,3,4,5,6-hexahydro-11(eq)-(3-oxo-3-phenylpropyl)-2,6-methano-3-benzazocine with 10.3 ml. of hydrazine hydrate and 4.2 g. of powdered potassium hydroxide in 51.5 ml. of diethylene glycol for four and a half hours at 205° C. and isolation of the product in the form of the free base gave 6.0 g. of 8-methoxy-3,6(eq),11(ax)-trimethyl-1,2,3,4,5,6-hexahydro-11(eq)-(3-phenylpropyl)-2,6-methano-3-benzazocine as a syrup which, on heating in a solution of 60 ml. of 48% aqueous hydrobromic acid and 30 ml. of glacial acetic acid, gave 3.2 g. of 8-hydroxy-3,6(eq),11(ax)-trimethyl-1,2,3,4,5,6-hexahydro-11(eq)-(3-phenylpropyl)-2,6-methano-3-benzazocine, m.p. 152°–156° C. (from ethyl acetate).

G. Heating 13.5 g. (0.03 mole) of 8-methoxy-3,6(eq),11(ax)-trimethyl-1,2,3,4,5,6-hexahydro-11(eq)-(3-oxo-5-phenylpentyl)-2,6-methano-3-benzazocine with 18.4 ml. of hydrazine hydrate and 7.5 g. of powdered potassium hydroxide in 92 ml. of diethylene glycol for two hours at 205° C. and isolation of the product in the form of the free base afforded 11.6 g. of 8-methoxy-3,6(eq),11(ax)-trimethyl-1,2,3,4,5,6-hexahydro-11(eq)-(5-phenylpentyl)-2,6-methano-3-benzazocine as a syrup which, on heating with 116 ml. of 48% aqueous hydrobromic acid, afforded 4.5 g. of 8-hydroxy-3,6(eq),11(ax)-trimethyl-1,2,3,4,5,6-hexahydro-11(eq)-(5-phenylpentyl)-2,6-methano-3-benzazocine, m.p. 140°–142° C. (from ethanol).

EXAMPLE 2

A. A solution of 8.0 g. (0.015 mole) of 8-methoxy-3,6(eq)-dimethyl-1,2,3,4,5,6-hexahydro-11(eq)-(3-oxooctyl)-2,6-methano-3-benzazocine p-toluenesulfonate in 40 ml. of 48% hydrobromic acid was heated under reflux for twenty minutes, then concentrated to dryness under reduced pressure, and the residual gum was dissolved in a solution of 50 ml. of water and excess 3 M sodium hydroxide. The pH of the clear solution was adjusted to 8.5–9.0, and the gum which separated crystallized to a solid which was collected and air-dried to give 5.4 g. of 8-hydroxy-3,6(eq)-dimethyl-1,2,3,4,5,6-hexahydro-11(eq)-(3-oxooctyl)-2,6-methano-3-benzazocine, m.p. 103°–107° C.

The latter (3.4 g., 0.01 mole) was heated in a solution containing 1.8 g. of 100% hydrazine hydrate, 2.4 g. of powdered potassium hydroxide and two drops of water in 25 ml. of diethylene glycol at 200°–210° C. for about four hours. The mixture was then diluted with water, the pH was adjusted to 7.0 with aqueous acid, and the tan solid which separated was collected and recrystallized from ethanol to give 3.3 g. of 8-hydroxy-3,6(eq)-dimethyl-1,2,3,4,5,6-hexahydro-11(eq)-octyl-2,6-methano-3-benzazocine, m.p. 129°–131° C.

Following a procedure similar to that described in Example 2A above, the following compounds of formula I were similarly prepared:

B. Heating a solution of 6.5 g. (0.017 mole) of 8-methoxy-3,6(eq),11(ax)-trimethyl-1,2,3,4,5,6-hexahydro-11(eq)-[3-oxo-3-(3-methylphenyl)-propyl]-2,6-methano-3-benzazocine in 150 ml. of 48% hydrobromic acid and isolation of the product in the form of the free base afforded 3.2 g. of 8-hydroxy-3,6(eq),11(ax)-trimethyl-1,2,3,4,5,6-hexahydro-11(eq)-[3-oxo-3-(3-methylphenyl)propyl]-2,6-methano-3-benzazocine, m.p. 203°–205° C. (from methanol). Heating the latter (4.5 g., 0.012 mole) in a solution of 10 ml. of 100% hydrazine hydrate and 2.8 g. of powdered potassium hydroxide in 25 ml. of diethylene glycol for five hours at 210° C. and isolation of the product in the form of the hydrochloride salt afforded 2.7 g. of 8-hydroxy-3,6(eq),11(ax)-trimethyl-1,2,3,4,5,6-hexahydro-11(eq)-[3-(3-methylphenyl)propyl]-2,6-methano-3-benzazocine hydrochloride, m.p. 265° C. (from methanol/diethyl ether).

C. Heating a solution of 9.2 g. (0.027 mole) of 8-methoxy-3,6(eq),11(ax)-trimethyl-1,2,3,4,5,6-hexahydro-11(eq)-(3-oxo-4-methylpentyl)-2,6-methano-3-benzazocine in 60 ml. of 48% aqueous hydrobromic acid afforded 9.8 g. of 8-hydroxy-3,6(eq),11(ax)-trimethyl-1,2,3,4,5,6-hexahydro-11(eq)-(3-oxo-4-methylpentyl)-2,6-methano-3-benzazocine as a viscous oil. The latter, on heating in a solution of 20 ml. of 100% hydrazine hydrate and 7.1 g. of powdered potassium hydroxide in 70 ml. of diethylene glycol for six and a half hours at 200°–220° C. and isolation of the product in the form of the ethanesulfonate salt, afforded 2.1 g. of 8-hydroxy-3,6(eq),11(ax)-trimethyl-1,2,3,4,5,6-hexahydro-11(eq)-(4-methylpentyl)-2,6-methano-3-benzazocine ethanesulfonate, m.p. 228°–232° C. (from acetone/diethyl ether).

EXAMPLE 3

A. A solution of 4.6 g. (0.011 mole) of 8-methoxy-3,6(eq),11(ax)-trimethyl-1,2,3,4,5,6-hexahydro-11(eq)-(3-oxononyl)-2,6-methano-3-benzazocine hydrochloride, 10 ml. of 100% hydrazine hydrate and 2.8 g. of powdered potassium hydroxide in 30 ml. of diethylene glycol was heated at 200°–210° C. for twenty-eight hours and then cooled and poured into 100 ml. of cold water. The pH was adjusted to about neutral, and the mixture was extracted two times with diethyl ether. The combined ether extracts were dried and taken to dryness, and the residue was dissolved in acetone and treated with an excess of ethereal hydrogen chloride. There was thus obtained 1.6 g. of 8-hydroxy-3,6(eq),11(ax)-trimethyl-1,2,3,4,5,6-hexahydro-11(eq)-nonyl-2,6-methano-3-benzazocine hydrochloride, m.p. 242°–245° C. (from acetone/diethyl ether).

B. Following a procedure similar to that described in Example 3A above, 3.9 g. (0.0096 mole) of 8-methoxy-3,6(eq),11(ax)-trimethyl-1,2,3,4,5,6-hexahydro-11(eq)-(3-oxooctyl)-2,6-methano-3-benzazocine hydrochloride was heated in a solution containing 10 ml. of 100% hydrazine hydrate and 2.6 g. of potassium hydroxide in 25 ml. of diethylene glycol at 200°–210° C. for twenty-four hours. There was thus obtained 1.7 g. of 8-hydroxy-3,6(eq),11(ax)-trimethyl-1,2,3,4,5,6-hexahydro-11(eq)-octyl-2,6-methano-3-benzazocine, m.p. 153°–155° C. (from hexane).

The 2-naphthalenesulfonate salt shows m.p. 210°–213° C. (from methanol/diethyl ether), and the fumarate shows m.p. 216°–220° C. (from methanol).

EXAMPLE 4

A. To a solution of 4.0 g. (0.012 mole) of 8-hydroxy-3,6(eq),11(ax)-trimethyl-1,2,3,4,5,6-hexahydro-11(eq)-octyl-2,6-methano-3-benzazocine in 50 ml. of DMF was added 560 mg. (0.013 mole) of a 57% mineral oil dispersion of sodium hydride, and the reaction mixture was stirred for one hour, then cooled in an ice bath and treated dropwise with 1.3 ml. of dimethyl sulfate. When addition was complete, the ice bath was removed, and the mixture was stirred at ambient temperature. The mixture was then poured into 200 ml. of water, the mixture was rendered strongly basic with sodium hydroxide and then extracted two times with diethyl ether. The combined ether extracts were washed with water, then with brine, dried over magnesium sulfate and taken to dryness to give an oil which was dissolved in ether and treated with an excess of ethereal hydrogen chloride. The resulting solid was recrystallized from ethanol/diethyl ether to give 1.7 g. of 8-methoxy-3,6(eq),11(ax)-trimethyl-1,2,3,4,5,6-hexahydro-11(eq)-octyl-2,6-methano-3-benzazocine hydrochloride, m.p. 198°–200° C.

B. It is contemplated that, by reaction of 8-hydroxy-3,6(eq),11(ax)-trimethyl-1,2,3,4,5,6-hexahydro-11(eq)-octyl-2,6-methano-3-benzazocine in DMF with sodium hydride and reaction of the resulting sodium salt with benzyl bromide using the procedure described above in Example 4A, there will be obtained 8-benzyloxy-3,6(eq),11(ax)-trimethyl-1,2,3,5,6-hexahydro-11(eq)-octyl-2,6-methano-3-benzazocine.

C. It is contemplated that, by reaction of ethyl 7-methoxy-1-methyl-4aα,5α-tetramethylene-1,2,3,4,4a,5,10,10a-octahydro-2,5-methanobenzo[g]quinoline-3-carboxylate (U.S. Pat. No. 4,100,164) with lithium diisopropylamide in tetrahydrofuran, followed by reaction of the resulting lithium salt with hexanoyl chloride, followed by heating the resulting ethyl 7-methoxy-1-methyl-3-(1-oxohexyl)-4aα,5α-tetramethylene-1,2,3,4,4a,5,10,10a-octahydro-2,5-methanobenzo[g]quinoline-3-carboxylate with formic acid in mesitylene, all according to the procedure described in U.S. Pat. No. 4,119,628, there will be obtained 8-methoxy-3-methyl-6(eq),11(ax)-tetramethylene-1,2,3,4,5,6-hexahydro-11(eq)-(3-oxooctyl)-2,6-methano-3-benzazocine; and that by heating the latter with hydrazine and potassium hydroxide in ethylene glycol at 200° C. for twenty-four hours using the procedure described above in Example 3A, there will be obtained 8-hydroxy-3-methyl-6(eq),11(ax)-tetramethylene-1,2,3,4,5,6-hexahydro-11(eq)-octyl-2,6-methano-3-benzazocine; and that by refluxing the latter in dimethoxymethane in the presence of a small amount of p-toluenesulfonic acid under a Soxhlet extractor containing 4A molecular sieves there will be obtained 8-methoxymethoxy-3-methyl-6(eq),11(ax)-tetramethylene-1,2,3,4,5,6-hexahydro-11(eq)-octyl-2,6-methano-3-benzazocine.

EXAMPLE 5

It is contemplated that by following a procedure similar to that described in Example 3A, 8-methoxy-3,6(eq),11(ax)-trimethyl-1,2,3,4,5,6-hexahydro-11(eq)-(3-oxo-5-cyclopentylpentyl)-2,6-methano-3-benzazocine will be reduced and demethylated to give 8-hydroxy-3,6(eq),11(ax)-trimethyl-1,2,3,4,5,6-hexahydro-11(eq)-(5-cyclopentylpentyl)-2,6-methano-3-benzazocine.

EXAMPLE 6

It is contemplated that by reacting 8-hydroxy-3,6(eq),11(ax)-trimethyl-1,2,3,4,5,6-hexahydro-11(eq)-octyl-2,6-methano-3-benzazocine with acetic anhydride, propionic anhydride or butyric anhydride in pyridine, or with acetyl chloride, propionyl chloride or butyryl chloride in the presence of a molar equivalent amount of triethylamine, there will be obtained, respectively, 8-acetoxy-3,6(eq),11(ax)-trimethyl-1,2,3,4,5,6-hexahydro-11(eq)-octyl-2,6-methano-3-benzazocine, 8-propionyloxy-3,6(eq),11(ax)-trimethyl-1,2,3,4,5,6-hexahydro-11(eq)-octyl-2,6-methano-3-benzazocine and 8-butyryloxy-3,6(eq),11(ax)-trimethyl-1,2,3,4,5,6-hexahydro-11(eq)-octyl-2,6-methano-3-benzazocine.

EXAMPLE 7

It is contemplated that by reducing 10-methoxy-3-benzyl-6(eq),11(ax)-dimethyl-1,2,3,4,5,6-hexahydro-11(eq)-(3-oxo-3-cyclopropylpropyl)-2,6-methano-3-benzazocine with hydrazine hydrate in the presence of potassium hydroxide in diethylene glycol using the procedure described above in Example 1A, there will be obtained 10-methoxy-3-benzyl-6(eq),11(ax)-dimethyl-1,2,3,4,5,6-hexahydro-11(eq)-(3-cyclopropylpropyl)-2,6-methano-3-benzazocine which, on catalytic reduction with hydrogen over Raney nickel, will afford 10-methoxy-6(eq),11(ax)-dimethyl-1,2,3,4,5,6-hexahydro-11(eq)-(3-cyclopropylpropyl)-2,6-methano-3-benzazocine; and that reaction of the latter in DMF in the presence of a molar equivalent amount of sodium carbonate with 1-(2-propenyl) bromide, 1-(2-methyl-2-propenyl) bromide and 1-(3-methyl-2-butenyl) bromide will afford, respectively, 10-methoxy-3-(2-propenyl)-6(eq), 11(ax)-dimethyl-1,2,3,4,5,6-hexahydro-11(eq)-(3-cyclopropylpropyl)-2,6-methano-3-benzazocine, 10-methoxy-3-(2-methyl-2-propenyl)-6(eq),11(ax)-dimethyl-1,2,3,4,5,6-hexahydro-11(eq)-(3-cyclopropylpropyl)-2,6-methano-3-benzazocine and 10-methoxy-3-(3-methyl-2-butenyl)-6(eq),11(ax)-dimethyl-1,2,3,4,5,6-hexahydro-11(eq)-(3-cyclopropylpropyl)-2,6-methano-3-benzazocine.

BIOLOGICAL TEST RESULTS

The compounds of formula I are generally active in the acetylcholine-induced abdominal constriction test (Ach), a primary analgesic screening test, and also in either the rat tail flick radiant thermal heat analgesic test (T.F.Ag.) or the rat tail flick phenazocine antagonist test (T.F.Ant.). Some of the species have also been tested and found active in the phenyl-p-quinone-induced writhing (PPQ) and antibradykinin (BK) tests, which are also primary analgesic screening procedures. Generally speaking, compounds which are active in the tail flick agonist test but inactive in the tail flick antagonist test are morphine-like analgesics, while species which are inactive in the tail flick agonist test but active in the tail flick antagonist test are narcotic antagonists.

the designation "±" in the Straub tail column indicating an occasional Straub tail observation at the dose indicated.

The finding of inactivity in a given test is indicated by the letter "I". All doses are expressed in milligrams per kilogram (mg./kg.) of the free base.

For purposes of comparison, corresponding data are given for morphine (designated "Ref."). The data show that, for the most part, the compounds of the invention have an activity profile similar to morphine (e.g. the species of Examples 1A, 1B, 1C, 1D, 1F, 2A, 2B, 2C and 4A), the species of Example 1F being exceptionally potent, and these species would thus be expected to have, like morphine, analgesic activity and significant accompanying addiction liability potential.

On the other hand, the species of Examples 1G and 3A, which are inactive in the tail flick agonist test but active in the tail flick antagonist test, would be expected to be narcotic antagonists.

The species of Example 3B is particularly noteworthy in that, although it possesses approximately the same magnitude of activity as morphine in each of the acetylcholine-induced abdominal constriction, the phenyl-p-quinone-induced writhing, the tail flick antagonist (morphine of course being known to be inactive as a narcotic antagonist) and the anti-bradykinin tests (actually about ten times as active as morphine in the latter), it is virtually inactive in the tail flick agonist test. This unique profile suggests that the species of Example 3B would be expected to be a very active strong analgesic with no narcotic antagonist activity and with minimal addiction liability potential.

| Ex. | Ach. | T.F. Ag. | T.F. Ant. | PPQ | BK | Straub | Dep. | Stim. |
|---|---|---|---|---|---|---|---|---|
| 1A | 0.23 | 27 | I/80 | — | — | +/2.0 | — | +/2.0 |
| 1B | 0.66 | 11(i.p.)* 38%/120(i.p.) | I/80(i.p.) | — | — | +/75 | — | +/75 |
| 1C | 0.86 | 5.3* | I/10 | — | — | +/75 | — | +/75 |
| 1D | 0.068 | 0.35* | I/80 | — | — | +/2.5 | — | +/2.5 |
| 1E | 0.11 | 0.47* | I/80 | — | — | +/2.5 | +/0.25 | +/2.5 |
| 1F | 0.0085 | 0.009–0.0013* | I/0.001 | — | — | +/0.1 | — | +/0.1 |
| 1G | 0%/25 20%/75 | I/20 | 0.046 | — | — | — | — | — |
| 2A | 6.5 | 60* | I/80 | — | — | +/25 | — | +/25 |
| 2B | 0.027 | 0.051* | I/0.001–0.01 | — | — | +/>0.1 | — | +/1.0,10.0 |
| 2C | 1.1 | 24 | I/1.0,10.0,80 | — | — | +/75 | — | +/75 |
| 3A | 11 | I/120(i.p.) | 2.2 | — | — | — | — | — |
| 3B | 0.76 10(p.o.) | 36%/240* | I/80 | 0.19 5.6(p.o.) | 0.20 10(p.o.) | +/25 | — | +/2.5 |
| Ref. | 0.60 5.0(p.o.) | 3.9 ± 0.5 79 ± 16(p.o.) | | 0.54 3.7(p.o.) | 2.3 | +/10 | | |
| 4A | 13%/10 20%/25 20%/75 22(p.o.) | I/20 59%/120(*i.p.) | I/20 | — | 40%/10(p.o.) | ±200(p.o.) | 13 | ±/200(p.o.) |

*Activity prevented by 1.0 mg./kg. (s.c.) of nalorphine

Further confirmation or morphine-like activity for the species of the invention is provided by the ability of nalorphine to prevent the analgesic activity of the test species.

Data so-obtained for the compounds, identified by reference to the preceeding examples and expressed either in terms of the ED$_{50}$ (or AD$_{50}$, Antagonist Doses$_{50}$, in the tail flick antagonist test) (mg./kg.) or in terms of percent inhibition, are given below. Unless noted otherwise by the designations p.o. (peroral) or i.p. (intraperitoneal), all drugs were administered subcutaneously. In addition, observations of the Straub tail reaction, depression or stimulation are indicated in the last three columns, the designation "+" indicating an unequivocal observation of the particular reaction, and

We claim:
1. A member of the group consisting of (A) compounds having the formula

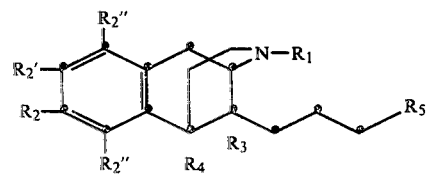

where $R_1$ is lower-alkyl, lower-alkenyl, cyclo-lower-alkyl-lower-alkyl, hydrogen or benzyl; one of $R_2$, $R_2'$, $R_2''$ and $R_2'''$ is hydroxy, lower-alkoxy, methoxymethoxy, benzyloxy or lower-alkanoyloxy, the others being hydrogen; $R_3$ is hydrogen or lower-alkyl; $R_4$ is lower-alkyl, or $R_3$ and $R_4$ together represent lower-alkylene, $(CH_2)_n$, where n is one of the integers 3 or 4; and $R_5$ is lower-alkyl containing from three to six carbon atoms, phenyl, phenyl-lower-alkyl, cyclo-lower-alkyl or cyclo-lower-alkyl-lower-alkyl, or such phenyl and phenyl-lower-alkyl groups substituted in the phenyl ring by a lower-alkyl group, and (B) acid-addition salts thereof with the proviso that $R_3$ and the group $(CH_2)_3R_5$ are dissimilar.

2. A compound according to claim 1 wherein $R_1$ is lower-alkyl, lower-alkenyl or cyclo-lower-alkyl -lower-alkyl; and one of $R_2$, $R_2'$, $R_2''$ and $R_2'''$ is hydroxy or lower-alkoxy.

3. A compound according to claim 2 where $R_1$ is lower-alkyl; $R_2$ is hydroxy or lower-alkoxy; $R_2'$, $R_2''$ and $R_2'''$ are each hydrogen; $R_3$ is hydrogen or lower-alkyl; and $R_4$ is lower-alkyl.

4. A compound according to claim 3 where $R_5$ is phenyl or phenyl-substituted in the phenyl ring by a lower-alkyl group.

5. A compound according to claim 3 where $R_5$ is phenyl-lower-alkyl or phenyl-lower-alkyl substituted in the phenyl ring by a lower-alkyl group.

6. A compound according to claim 3 where $R_5$ is cyclo-lower-alkyl.

7. A compound according to claim 3 where $R_5$ is cyclo-lower-alkyl-lower-alkyl.

8. 8-Hydroxy-3,6(eq)-dimethyl-1,2,3,4,5,6-hexahydro-11(eq)-octyl-2,6-methano-3-benzazocine according to claim 3.

9. 8-Hydroxy-3,6(eq),11(ax)-trimethyl-1,2,3,4,5,6-hexahydro-11(eq)-octyl-2,6-methano-3-benzazocine according to claim 3.

10. 8-Hydroxy-3,6(eq),11(ax)-trimethyl-1,2,3,4,5,6-hexahydro-11(eq)-nonyl-2,6-methano-3-benzazocine according to claim 3.

11. 8-Hydroxy-3,6(eq)-dimethyl-1,2,3,4,5,6-hexahydro-11(eq)-heptyl-2,6-methano-3-benzazocine according to claim 3.

12. 8-Hydroxy-3,6(eq)-dimethyl-1,2,3,4,5,6-hexahydro-11(eq)-(6-methylheptyl)-2,6-methano-3-benzazocine according to claim 3.

13. 8-Hydroxy-3,6(eq),11(ax)-trimethyl-1,2,3,4,5,6-hexahydro-11(eq)-(6-methylheptyl)-2,6-methano-3-benzazocine according to claim 3.

14. 8-Hydroxy-3,6(eq),11(ax)-trimethyl-1,2,3,4,5,6-hexahydro-11(eq)-heptyl-2,6-methano-3-benzazocine according to claim 3.

15. 8-Hydroxy-3,6(eq),11(ax)-trimethyl-1,2,3,4,5,6-hexahydro-11(eq)-hexyl-2,6-methano-3-benzazocine according to claim 3.

16. 8-Methoxy-3,6(eq),11(ax)-trimethyl-1,2,3,5,6-hexahydro-11(eq)-octyl-2,6-methano-3-benzazocine according to claim 3.

17. 8-Hydroxy-3,6(eq),11(ax)-trimethyl-1,2,3,4,5,6hexahydro-11(eq)-(4-methylpentyl)-2,6-methano-3-benzazocine according to claim 3.

18. 8-Hydroxy-3,6(eq),11(ax)-trimethyl-1,2,3,4,5,6-hexahydro-11(eq)-(3-phenylpropyl)-2,6-methano-3-benzazocine according to claim 4.

19. 8-Hydroxy-3,6(eq),11(ax)-trimethyl-1,2,3,4,5,6-hexahydro-11(eq)-[3-(3-methylphenyl)propyl]-2,6-methano-3-benzazocine according to claim 4.

20. 8-Hydroxy-3,6(eq),11(ax)-trimethyl-1,2,3,4,5,6-hexahydro-11(eq)-(5-phenylpentyl)-2,6-methano-3-benzazocine according to claim 5.

* * * * *

UNITED STATES PATENT AND TRADEMARK OFFICE
CERTIFICATE OF CORRECTION

PATENT NO. : 4,208,523
DATED : June 17, 1980
INVENTOR(S) : William F. Michne and Thomas R. Lewis It is certified that error appears in the above-identified patent and that said Letters Patent are hereby corrected as shown below:

Column 1, lines 55-56, change "cycloalkyl-lower-alkyl" to read --cyclo-lower-alkyl-lower-alkyl--.

Column 2, lines 1-9, change formula I to appear as:

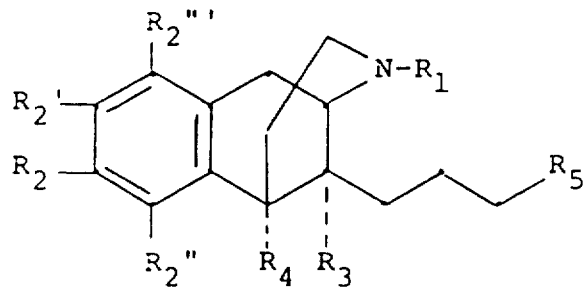

UNITED STATES PATENT AND TRADEMARK OFFICE
CERTIFICATE OF CORRECTION

PATENT NO. : 4,208,523

DATED : June 17, 1980

INVENTOR(S) : William F. Michne and Thomas R. Lewis

It is certified that error appears in the above-identified patent and that said Letters Patent are hereby corrected as shown below:

Page 2 of 3

Column 3, lines 1-9, change formula II to appear as:

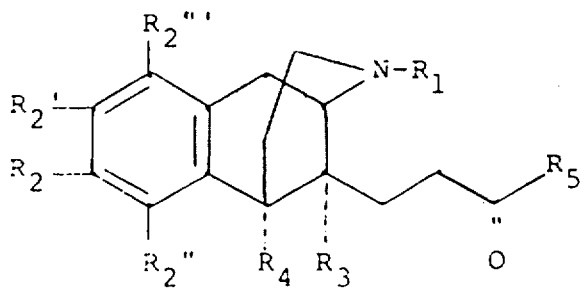

Column 12, lines 60-68, change the formula to appear as:

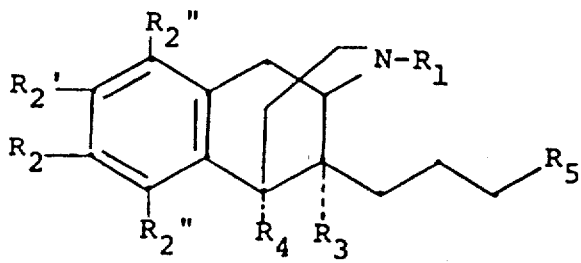

UNITED STATES PATENT AND TRADEMARK OFFICE
CERTIFICATE OF CORRECTION

PATENT NO. : 4,208,523

DATED : June 17, 1980

INVENTOR(S) : William F. Michne and Thomas R. Lewis

It is certified that error appears in the above-identified patent and that said Letters Patent are hereby corrected as shown below:

Column 14, line 22, Claim 16, change "1,2,3,5,6" to read 1,2,3,4,5,6".

Column 14, line 26, Claim 17, change "1,2,3,4,5,6hexahydro" to read --1,2,3,4,5,6-hexahydro--.

Signed and Sealed this

Second Day of November 1982

[SEAL]

Attest:

GERALD J. MOSSINGHOFF

Attesting Officer    Commissioner of Patents and Trademarks